US009558589B2

(12) United States Patent
Itai

(10) Patent No.: US 9,558,589 B2
(45) Date of Patent: Jan. 31, 2017

(54) MEDICAL IMAGE DISPLAY APPARATUS, METHOD, AND PROGRAM

(71) Applicant: FUJIFILM Corporation, Tokyo (JP)

(72) Inventor: Yoshinori Itai, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 142 days.

(21) Appl. No.: 14/637,547

(22) Filed: Mar. 4, 2015

(65) Prior Publication Data

US 2015/0178989 A1 Jun. 25, 2015

Related U.S. Application Data

(63) Continuation of application No. PCT/JP2013/005326, filed on Sep. 9, 2013.

(30) Foreign Application Priority Data

Sep. 12, 2012 (JP) ................................ 2012-200429

(51) Int. Cl.
    *G06K 9/00* (2006.01)
    *G01V 5/00* (2006.01)
    (Continued)

(52) U.S. Cl.
    CPC ............. *G06T 19/003* (2013.01); *A61B 5/055* (2013.01); *A61B 6/03* (2013.01); *A61B 6/463* (2013.01);
    (Continued)

(58) Field of Classification Search
    None
    See application file for complete search history.

(56) References Cited

U.S. PATENT DOCUMENTS 5,611,025 A * 3/1997 Lorensen ............. G09B 23/285
                                                    345/419
5,891,030 A * 4/1999 Johnson ................. A61B 6/032
                                                    128/920

(Continued)

FOREIGN PATENT DOCUMENTS

JP 2004-283373 A 10/2004
JP 2007-501675 A 2/2007

(Continued)

OTHER PUBLICATIONS

Hong et al. "Virtual Voyage: Interactive Navigation in the Human Colon"; Proceedings of the 24th annual conference on Computer graphics and interactive techniques; pp. 27-34; Year of Publication: 1997.*

(Continued)

*Primary Examiner* — Randolph I Chu
(74) *Attorney, Agent, or Firm* — Sughrue Mion, PLLC

(57) ABSTRACT

A medical image display apparatus includes a three-dimensional image obtaining unit that obtains a three-dimensional image of a subject, a tubular tissue region obtaining unit that obtains a tubular tissue region representing a tubular tissue of the subject from the three-dimensional image, an endpoint identification unit that identifies, if the tubular tissue region obtained by the tubular tissue region obtaining unit is separated, each endpoint of the two tubular tissue regions connecting to the separating portion, a cross-sectional image generation unit that generates a cross-sectional image that includes the two endpoints identified by the endpoint identification unit, a display control unit that displays the cross-sectional image generated by the cross-sectional image generation unit and a three-dimensional image of the tubular tissue region, and a route receiving unit that receives input of a route connecting the two tubular tissue regions.

11 Claims, 5 Drawing Sheets

(51) Int. Cl.
*G06T 19/00* (2011.01)
*A61B 6/03* (2006.01)
*A61B 5/055* (2006.01)
*A61B 6/00* (2006.01)
*G06T 7/60* (2006.01)
*G06T 7/00* (2006.01)
*G06T 15/08* (2011.01)
*A61B 1/31* (2006.01)

(52) U.S. Cl.
CPC .......... *A61B 6/5223* (2013.01); *G06T 7/0012* (2013.01); *G06T 7/608* (2013.01); *G06T 15/08* (2013.01); *G06T 19/00* (2013.01); *A61B 1/31* (2013.01); *A61B 6/466* (2013.01); *A61B 6/50* (2013.01); *A61B 6/5205* (2013.01); *G06T 2207/10081* (2013.01); *G06T 2207/30028* (2013.01); *G06T 2207/30172* (2013.01); *G06T 2210/41* (2013.01); *G06T 2219/028* (2013.01)

(56) References Cited

U.S. PATENT DOCUMENTS

| | | | | |
|---|---|---|---|---|
| 6,343,936 | B1* | 2/2002 | Kaufman | G06K 9/209 |
| | | | | 128/920 |
| 6,694,163 | B1* | 2/2004 | Vining | G06T 17/00 |
| | | | | 128/920 |
| 6,928,314 | B1* | 8/2005 | Johnson | G06T 7/606 |
| | | | | 128/920 |
| 7,324,104 | B1* | 1/2008 | Bitter | G06T 7/0081 |
| | | | | 345/419 |
| 7,369,691 | B2 | 5/2008 | Kondo et al. | |
| 7,711,163 | B2* | 5/2010 | Geiger | A61B 5/4255 |
| | | | | 382/128 |
| 9,401,047 | B2* | 7/2016 | Bogoni | G06T 19/00 |
| 2005/0048456 | A1 | 3/2005 | Chefd'Hotel et al. | |
| 2005/0261550 | A1* | 11/2005 | Akimoto | A61B 1/00009 |
| | | | | 600/117 |
| 2009/0054729 | A1 | 2/2009 | Mori et al. | |
| 2012/0053408 | A1* | 3/2012 | Miyamoto | G06T 19/20 |
| | | | | 600/109 |
| 2014/0161331 | A1* | 6/2014 | Cohen | G06T 5/003 |
| | | | | 382/128 |

FOREIGN PATENT DOCUMENTS

JP 2011-024913 A 2/2011
WO 2007/129616 A1 11/2007

OTHER PUBLICATIONS

Communication dated Apr. 22, 2016, issued by the Canadian Intellectual Property Office in corresponding Canadian Application No. 2,884,341.
International Search Report for PCT/JP2013/005326 dated Dec. 24, 2013.
Communication dated Jan. 12, 2016 from the Australian Intellectual Property Office in counterpart application No. 2013317199.
Communication dated Mar. 22, 2016, from the European Patent Office in counterpart European Application No. 13836430.2.

* cited by examiner

MEDICAL IMAGE DISPLAY APPARATUS, METHOD, AND PROGRAM

CROSS-REFERENCE TO RELATED APPLICATIONS

This application is a Continuation of PCT International Application No. PCT/JP2013/005326 filed on Sep. 9, 2013, which claims priority under 35 U.S.C. §119 (a) to Japanese Patent Application No. 2012-200429 filed on Sep. 12, 2012. Each of the above applications is hereby expressly incorporated by reference, in its entirety, into the present application.

BACKGROUND OF THE INVENTION

Technical Field

The present invention relates to a medical image display apparatus, method, and program that extracts a tubular tissue region from a three-dimensional image of a subject and displays a three-dimensional image of the tubular issue region.

Background Art

Recently, it has been practiced that tubular tissues, such as large intestines, small intestines, bronchi, blood vessels, and the like, are extracted from three-dimensional images captured by modalities, such as CT (Computed Tomography) systems and the like, and three-dimensional images of the extracted tubular tissues are used in image diagnosis.

For example, in large intestine colonography, a technique is proposed in which, based on a three-dimensional image of a large intestine region, a route of an endoscope passing through the large intestine region is determined, then a virtual endoscopic image is generated which is similar to an image captured by an endoscope by moving the viewpoint along the determined route and actually imaging from each viewpoint, and the route to a target point is navigated by displaying the virtual endoscopic image.

SUMMARY OF THE INVENTION

Here, when extracting a three-dimensional image of a large intestine region, if, for example, a residue or an obstruction is present, the CT value of that portion differs from the CT value of the large intestine region, i. e., the CT value of air, and that portion is not extracted as the large intestine region, thereby often resulting in that the large intestine region is separated into a plurality of regions, as shown in FIG. 8. In the case of the example shown in FIG. 8, the portion between the point P4 and the point P5, and the portion between the point P2 and the point P3 are separating portions.

If the large intestine region is extracted in a separate manner as described above, the endoscopic route is also separated and a virtual endoscope image of the separating portion cannot be generated and displayed. Consequently, it is conceivable, for example, to determine the route between two separate large intestine regions by connecting the two regions with a straight or curved line according to a predetermined rule. But the large intestine is a soft tissue and is deformed largely according to the bodily posture of the patient when imaging is performed, so that it is very unlikely that the foregoing straight or curved line corresponds to the actual large intestine route.

Japanese Unexamined Patent Publication No. 2004-283373 discloses that, when extracting a core line of a blood vessel, the once automatically extracted core line is corrected by the user in a two-dimensional image. But it is difficult to accurately correct the core line by such core line correction in a two-dimensional image, because it is difficult to understand a three-dimensional structure of the actual blood vessel.

Japanese Unexamined Patent Publication No. 2004-283373 further proposes a method that, when extracting a core line of a blood vessel, a passing point of the core line is newly added if an obstruction is present and the core line including the passing point is re-extracted.

But, as a core line is re-extracted based on the point newly added by the user according to a predetermined rule also in this method, the core line is not always extracted accurately in the case of a tissue that deforms largely, such as a large intestine.

In view of the circumstances described above, it is an object of the present invention to provide a medical image display apparatus, method, and program capable of editing a route in the separating portion simply and accurately even if a tubular tissue region, such as a large intestine region, is extracted as a plurality of separate regions.

A medical image display apparatus of the present invention is an apparatus, including a three-dimensional image obtaining unit that obtains a three-dimensional image of a subject, a tubular tissue region obtaining unit that obtains a tubular tissue region representing a tubular tissue of the subject from the three-dimensional image obtained by the three-dimensional image obtaining unit, an endpoint identification unit that identifies, if the tubular tissue region obtained by the tubular tissue region obtaining unit is separated, each endpoint of the two tubular tissue regions connecting to the separating portion, a cross-sectional image generation unit that generates a cross-sectional image that includes the two endpoints identified by the endpoint identification unit, a display control unit that displays the cross-sectional image generated by the cross-sectional image generation unit and a three-dimensional image of the tubular tissue region, and a route receiving unit that receives input of a route connecting between the two tubular tissue regions.

In the medical image display apparatus described above, the cross-sectional image generation unit may be a unit that generates a cross-sectional image whose normal vector gives a maximum inner product with a normal vector of a projection plane of the three-dimensional image of the tubular tissue region.

Further, the endpoint identification unit may be a unit that identifies points inputted by the user using an input device as the two endpoints.

Still further, the endpoint identification unit may be a unit that automatically detects and identifies the two endpoints.

Further, the display control unit may be a unit that displays the cross-sectional image and the three-dimensional image of the tubular tissue region superimposed on top of each other.

Further, the display control unit may be a unit that displays the cross-sectional image and the three-dimensional image of the tubular tissue region side-by-side.

Still further, the cross-sectional image generation unit may be a unit that generates, as the cross-sectional image, a CPR (Curved Planar Reformation) image using the route received by the route receiving unit as a core line.

Further, the route receiving unit may be a unit that receives the input of a route connecting the two tubular tissue regions a plurality of times, and the cross-sectional image generation unit may be a unit that generates a CPR image with respect to each input of a route.

Still further, the tubular tissue region may be a large intestine, a small intestine, a bronchus, or a blood vessel.

A medical image display method of the present invention is a method, including the steps of obtaining a three-dimensional image of a subject, obtaining a tubular tissue region representing a tubular tissue of the subject from the obtained three-dimensional image, if the obtained tubular tissue region is separated, identifying each endpoint of the two tubular tissue regions connecting to the separating portion, generating a cross-sectional image that includes the identified two endpoints, displaying the generated cross-sectional image and a three-dimensional image of the tubular tissue region, and receiving input of a route connecting between the two tubular tissue regions.

A medical image display program of the present invention is a program for causing a computer to function as a three-dimensional image obtaining unit that obtains a three-dimensional image of a subject, a tubular tissue region obtaining unit that obtains a tubular tissue region representing a tubular tissue of the subject from the three-dimensional image obtained by the three-dimensional image obtaining unit, an endpoint identification unit that identifies, if the tubular tissue region obtained by the tubular tissue region obtaining unit is separated, each endpoint of the two tubular tissue regions connecting to the separating portion, a cross-section image generation unit that generates a cross-sectional image that includes the two endpoints identified by the endpoint identification unit, a display control unit that displays the cross-sectional image generated by the cross-section generation unit and a three-dimensional image of the tubular tissue region, and a route receiving unit that receives input of a route connecting between the two tubular tissue regions.

According to the medical image display apparatus, method, and program of the present invention, a tubular tissue region representing a tubular tissue of a subject is obtained from a three-dimensional image of the subject, then, if the obtained tubular tissue region is separated, each endpoint of the two tubular tissue regions connecting to the separating portion is identified, a cross-sectional image that includes the identified two endpoints is generated, the generated cross-sectional image and a three-dimensional image of the tubular tissue region are displayed, and input of a route connecting between the two tubular tissue regions is received. This allows the user to input a route by understand the structure of the separating portion described above by the cross-sectional image, while understanding the three-dimensional structure of the tubular tissue region by viewing the three-dimensional image, whereby the user may edit the route in the separating portion easily and accurately.

When generating the cross-sectional image, if a cross-sectional image whose normal vector gives a maximum inner product with a normal vector of the projection plane of the three-dimensional image of the tubular tissue region is generated, the visualization of the tubular tissue region in the cross-sectional image from the direction of the viewpoint of the user may be improved.

Further, when generating the cross-sectional image, if a CPR image is generated as the cross-sectional image using the route inputted by the user as a core line, and a CPR image is regenerated with respect to each input of a route, the user may select and display an optimum CPR image for route input by confirming each CPR image.

DESCRIPTION OF EMBODIMENTS

Figure 1:
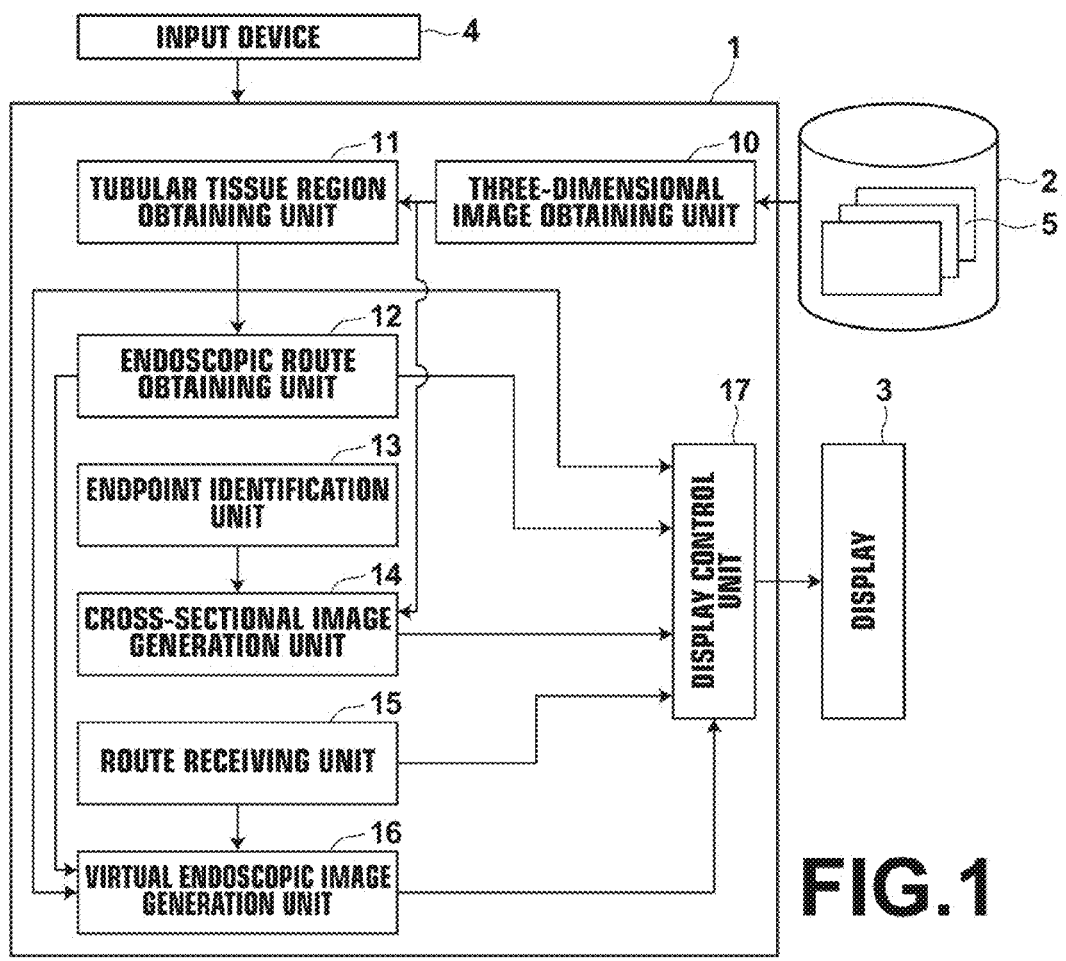
FIG. 1 is a block diagram of an endoscopic image diagnosis support system that uses one embodiment of the medical image display apparatus of the present invention, schematically illustrating the configuration thereof.

Hereinafter, an endoscopic image diagnosis support system that uses one embodiment of the medical image display apparatus, method, and program of the present invention will be described in detail with reference to the accompanying drawings. FIG. 1 is a block diagram of the endoscopic image diagnosis support system that uses a first embodiment.

As illustrated in FIG. 1, the present endoscopic image diagnosis support system includes an endoscopic image diagnosis support apparatus 1, a three-dimensional image storage server 2, a display 3, and an input device 4.

The endoscopic image diagnosis support apparatus 1 is a computer on which a medical image display program of the present embodiment is installed. The endoscopic image diagnosis support apparatus 1 includes a central processing unit (CPU) and storage devices, such as a semiconductor memory, a hard disk in which the medical image display program of the present embodiment is installed, a SSD (Solid State Drive), and the like. By theses hardware devices, a three-dimensional image obtaining unit 10, a tubular tissue region obtaining unit 11, an endoscopic route obtaining unit 12, an endpoint identification unit 13, a cross-sectional image generation unit 14, a route receiving unit 15, a virtual endoscopic image generation unit 16, and a display control unit 17 are formed, as illustrated in FIG. 1. Then, each unit will operate when the medical image display program of the present embodiment installed in the hard disk is executed by the central processing unit.

The three-dimensional image obtaining unit 10 obtains a three-dimensional image 5 of a subject captured in advance before surgery or examination. The three-dimensional image 5 may be, for example, volume data reconstructed from slice data outputted from a CT system, a MRI (Magnetic Resonance Imaging) system, or the like, volume data outputted from a MS (Multi Slice) CT system or a cone beam CT system, and other similar data. The three-dimensional image 5 is stored in the three-dimensional image storage server 2 in advance with identification information of the subject, and the three-dimensional image obtaining unit 10 reads out a three-dimensional image 5 corresponding to the identification information inputted from the input device 4 from the three-dimensional image storage server 2. The tubular tissue region obtaining unit 11 receives the three-dimensional image 5 obtained by the three-dimensional image obtaining unit 10 and obtains a tubular tissue region of the subject from the received three-dimensional image 5. The tubular tissue may be, for example, a large intestine, a small intestine, a bronchus, or a blood vessel, such as a coronary artery, but not limited to these and other tubular tissues may also be obtained. In the present embodiment, a large intestine shape will be extracted and obtained.

A specific method of extracting a large intestine region is as follows. First, a plurality of axial images which is perpendicular to the body axis is generated based on the three-dimensional image 5 and the outside body area is separated from the inside body area on the basis of body surface by a known method with respect to each axial image. For example, binarization processing is performed on inputted axial image, a contour is extracted by contour extraction processing, and the inside of the extracted contour is extracted as the inside (human) body area. Next, threshold binarization processing is performed on an axial image of inside body area and a large intestine candidate in each axial image is extracted. More specifically, binarization processing is performed by setting a threshold value corresponding to the CT value of air (e.g., −600 or less), since air is contained in the large intestine tube, and an air region within the body of each axial image is extracted as a large intestine candidate. Finally, a large intestine region is obtained by extracting only a portion of the extracted inside body area where large intestine candidates are connected between each of the axial image data. Note that the method of extracting a large intestine region is not limited to that described above, and other known methods, such as Region Growing method, Level Set method, and the like may also be used.

The endoscopic route obtaining unit 12 extracts a tree-structure of the large intestine by thinning the three-dimensional image of large intestine region obtained in the manner described above and deducing the center line of the large intestine, and obtains the tree structure as the endoscopic route. For the thinning processing, any known method may be employed. For example, the methods described in the following literature may be used: M. Yasue et al., "Thinning Algorithms for Three-Dimensional Gray Images and Their Application to Medical Images with Comparative Evaluation of Performance", Journal of The Institute of Electronics, Information and Communication Engineers, J79-D-II, No. 10, pp. 1664-1674, 1996, T. Saito et al., "An Improvement of Three Dimensional Thinning Method Using a Skeleton Based on the Euclidean Distance Transformation-A Method to Control Spurious Branches", Journal of The Institute of Electronics, Information and Communication Engineers, Vol. J84-D-II, No. 8, pp. 1628-1632, 2001, and the like.

The endoscopic route obtaining unit 12 outputs the endoscopic route information obtained in the manner as described above to the display control unit 17, and the endoscopic route is displayed on the display 3 by the display control unit 17.

The endpoint identification unit 13 identifies, if the large intestine region and the endoscopic route obtained in the manner as described above are separated, each endpoint of the two large intestine regions connecting to the separating portion. More specifically, in the present embodiment, if the large intestine region displayed on the display 3 is separated, each point of the two large intestine regions adjacent to the separating portion is selected by the user with the use of the input device 4. More specifically, for example, an endpoint of the endoscopic route displayed on the display 3 is selected. Then, the endpoint identification unit 13 obtains position information of the point selected by the input device 4 and identifies two endpoints of two separate large intestine regions. Then, the endpoint identification unit 13 outputs the position information of the two endpoints to the cross-sectional image generation unit 14.

The cross-sectional image generation unit 14 generates a cross-sectional image that includes the two endpoints outputted from the endpoint identification unit 13 based on the three-dimensional image obtained by the three-dimensional image obtaining unit 10. Then, the cross-sectional image generation unit 14 outputs the generated cross-sectional image to the display control unit 17 and the cross-sectional image is displayed on the display 3 by the display control unit 17. A specific cross-sectional image generation method will be described later in detail.

The route receiving unit 15 receives input of a route connecting between two separate large intestine regions displayed on the display 3. More specifically, in the present embodiment, a route connecting between two separate large intestine regions is inputted in the cross-sectional image displayed on the display 3 by the user with the use of the input device 4, and the route receiving unit 15 obtains information of the inputted route. Then, the route receiving unit 15 outputs the information of the inputted route to the display control unit 17 and the route described above is displayed on the display 3 by the display control unit 17.

The virtual endoscopic image generation unit 16 receives the three-dimensional image of the large intestine region obtained by the tubular tissue region obtaining unit 11, the endoscopic route obtained by the endoscopic route obtaining unit 12, and the route inputted to the route receiving unit 15 by the user. Then, the virtual endoscopic image generation unit 16 generates a virtual endoscopic image with a given point on the line that combines the endoscopic route and the route inputted by the user as the viewpoint. More specifically, the virtual endoscopic image generation unit 16 obtains, as the virtual endoscopic image, a projection image generated by a central projection method in which three-dimensional images on a plurality of visual lines extending from the foregoing viewpoint is projected onto a predetermined projection plane. A specific central projection method that can be used may be, for example, the known volume rendering method and the like. Note that, it is assumed that the angle of field (range of visual lines) and the center of visual field (center in the projection direction) are set in advance by the user input or the like.

Then, the virtual endoscopic image generation unit 16 outputs the virtual endoscopic image generated in the foregoing manner to the display control unit 17 and the virtual endoscopic image is displayed on the display 3 by the display control unit 17.

The display control unit 17 receives the three-dimensional image of the large intestine obtained by the tubular tissue region obtaining unit 11, performs volume rendering or surface rendering on the three-dimensional image, and displays a three-dimensional image of the entire large intestine on the display 3 by the voxel model or the surface model. In addition, the display control unit 17 receives the endoscopic route obtained by the endoscopic route obtaining unit 12 and the route obtained by the route receiving unit 15, and displays these routes superimposed on the three-dimensional image of the entire large intestine.

Further, the display control unit 17 displays the cross-sectional image generated in the cross-sectional image generation unit 14 and the three-dimensional image of the entire large intestine on the display 3 on top of each other. Still further, the display control unit 17 displays the virtual endoscopic image generated in the virtual endoscopic image generation unit 16 on the display 3.

The input device 4 receives user input of foregoing various types of information and includes, for example, a pointing device, such as a keyboard, a mouse, and the like.

Figure 2:
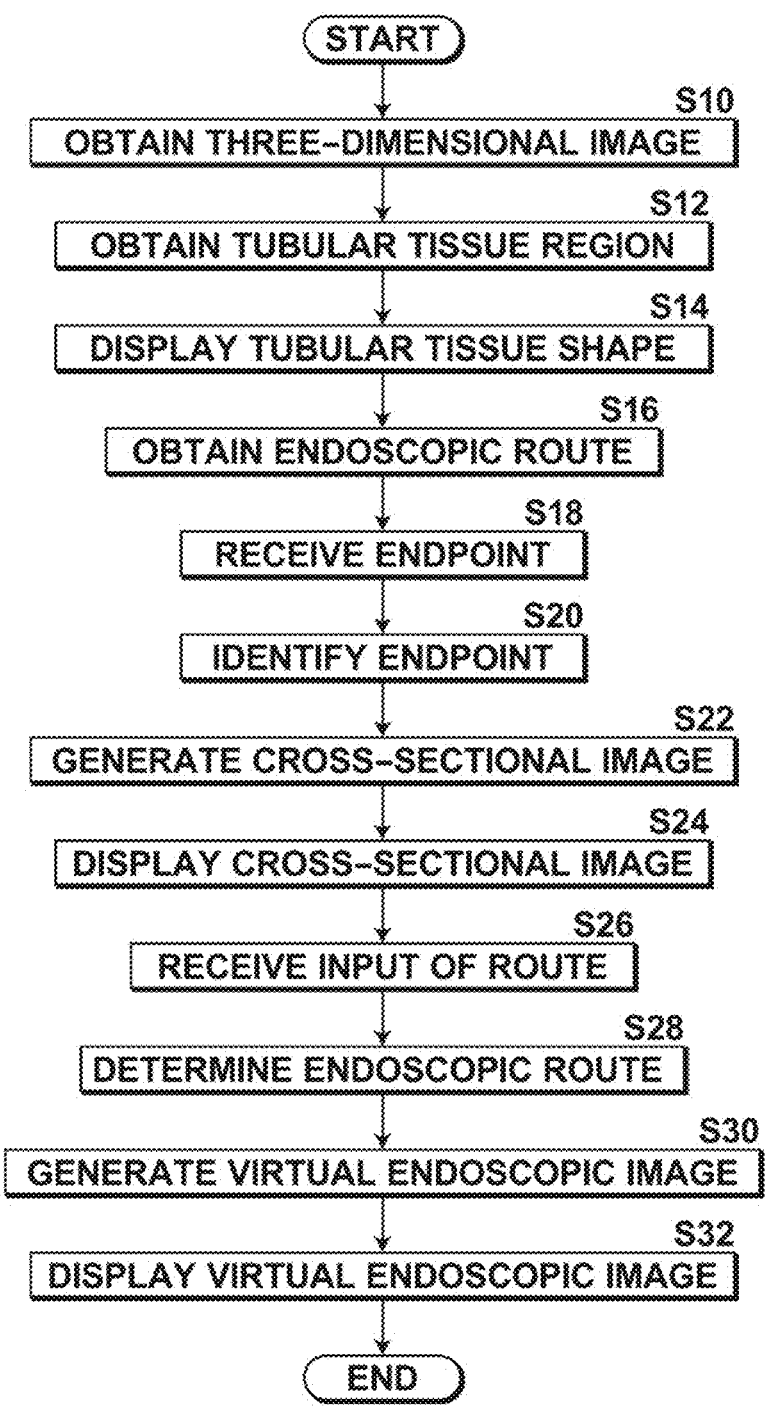
FIG. 2 is a flowchart for explaining an operation of the endoscopic image diagnosis support system that uses one embodiment of the medical image display apparatus of the present invention.

An operation of the endoscopic image diagnosis support system of the present embodiment will now be described with reference to the flowchart shown in FIG. 2.

First, identification information of a subject is inputted at the input device 4, and the three-dimensional image obtaining unit 10 of the endoscopic image diagnosis support apparatus 1 reads out and obtains a three-dimensional image 5 corresponding to the inputted subject identification information from the three-dimensional image storage server 2 (S10).

The three-dimensional image obtained by the three-dimensional image obtaining unit 10 is inputted to the tubular tissue region obtaining unit 11, and the tubular tissue region obtaining unit 11 extracts and obtains a large intestine region based on the inputted three-dimensional image (S12).

Figure 3:
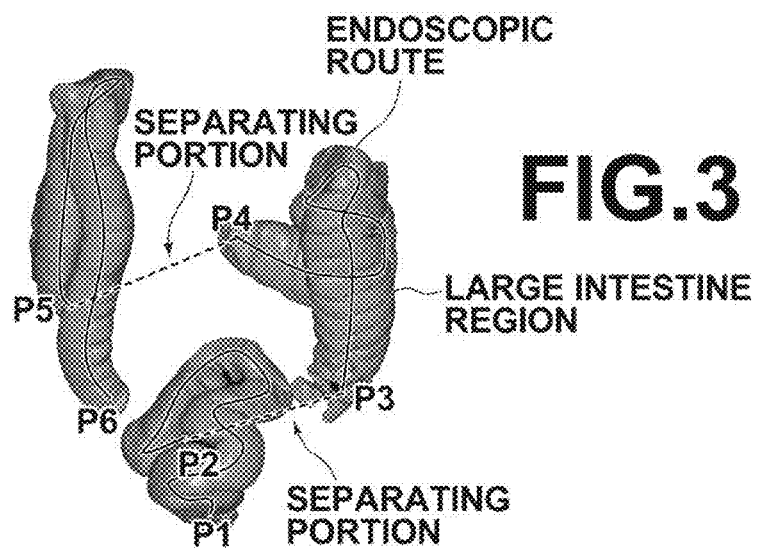
FIG. 3 is a drawing illustrating an example of a three-dimensional large intestine image and an endoscopic route.

The three-dimensional image of the large intestine region obtained by the tubular tissue region obtaining unit 11 is outputted to the display control unit 17 and the display control unit 17 displays the three-dimensional image of the entire large intestine region on the display 3 (S14). FIG. 3 illustrates one example of a large intestine region displayed on the display 3.

Further, the three-dimensional image of the large intestine region obtained by the tubular tissue region obtaining unit 11 is inputted to the endoscopic route obtaining unit 12, and the endoscopic route obtaining unit 12 obtains an endoscopic route based on the inputted three-dimensional image of the large intestine region in the manner as described above (S16). Then the endoscopic route obtained by the endoscopic route obtaining unit 12 is outputted to the display control unit 17, and the display control unit 17 displays the inputted endoscopic route on the display 3. At this time, the display control unit 17 displays the endoscopic route superimposed on the three-dimensional image of the large intestine region. FIG. 3 illustrates one example of an endoscopic route displayed on the display 3.

Here, as described above, when a three-dimensional image of a large intestine region is extracted and an endoscopic route is obtained based on the large intestine region, the large intestine region is sometimes separated into a plurality of regions, and in such a case, an accurate endoscopic route cannot be obtained for a separating portion. In the example shown in FIG. 3, the portion between the endpoints P4 and P5 on the endoscopic route and the portion between the endpoints P2 and P3 on the endoscopic route are separated.

Therefore, in the present embodiment, user input of an endoscopic route in the separating portion shown in FIG. 3 is received. More specifically, the following processing is performed.

First, the separating portion is confirmed by the user who has observed the three-dimensional image of the large intestine region displayed on the display 3 and each endpoint of the two large intestine regions adjacent to the separating portion is inputted by the user with the use of the input device 4 (S18). More specifically, in the present embodiment, the endpoints P4 and P5, and the endpoints P2 and P3 on the endoscopic route are selected using the input device 4. Then, position information of the endpoints P4 and P5 and endpoints P2 and P3 is obtained by the endpoint identification unit 13, and the endpoint identification unit 13 identifies the inputted position information as the position information of endpoints of the two separate large intestine regions (S20).

Figure 4:
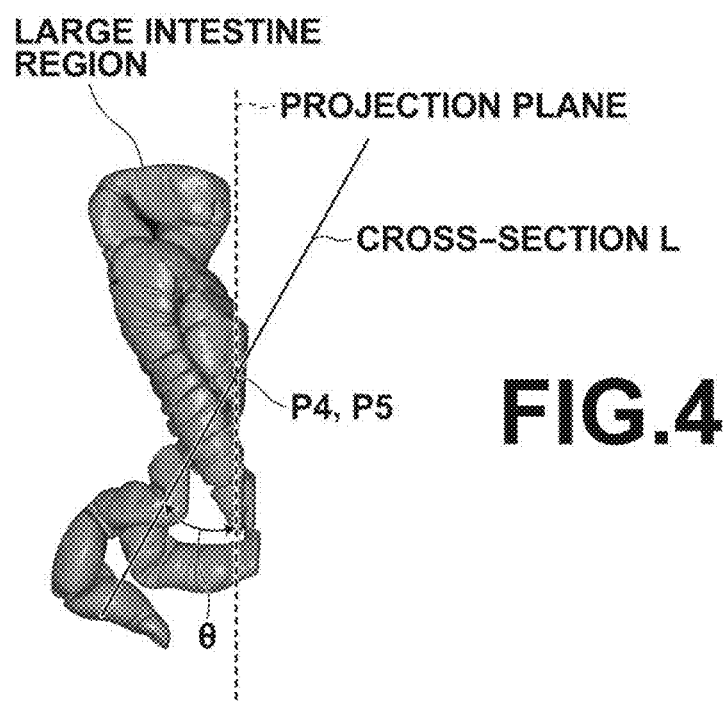
FIG. 4 is a drawing for explaining a cross-sectional image generation method.
Figure 5:
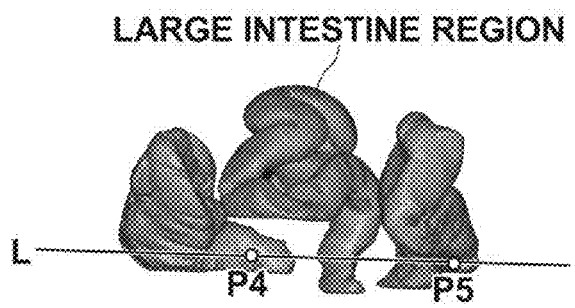
FIG. 5 is a drawing of the three-dimensional large intestine image shown in FIG. 4 viewed from above.

Next, the position information of the endpoints identified by the endpoint identification unit 13 is inputted to the cross-sectional image generation unit 14, and the cross-sectional image generation unit 14 generates a cross-sectional image that includes the inputted position information of the endpoints using the three-dimensional subject image 5 outputted from the three-dimensional image obtaining unit 10 (S22). More specifically, for example, if position information of the endpoints P4 and P5 is obtained, the cross-sectional image generation unit 14 generates a cross-sectional image that includes the endpoints P4 and P5 and whose normal vector gives a maximum inner product with a normal vector of a projection plane of the three-dimensional image of the large intestine region. FIG. 4 shows a case in which the straight line connecting the endpoints P4 and P5 is present on the projection plane described above, and in this case, a cross-sectional image whose angle θ formed with the projection plane is minimal is generated among those that include the endpoints P4 and P5. In the case of the example shown in FIG. 4, an image of a cross-section L with θ being 0°, that is, an image of a cross-section L whose normal vector is parallel to a normal vector of the projection plane is generated. Note that FIG. 5 is a view of the large intestine region image shown in FIG. 4 viewed from above.

Note that the two endpoints are not always present on the projection plane; either one of them may not be present on the projection plane or neither of them may present on the projection plane. Therefore, the cross-sectional image generation unit 14 will generate a cross-sectional image that includes the two endpoints and whose normal vector gives a maximum inner product with a normal vector of the projection plane of the three-dimensional image of the large intestine region. Such cross-sectional image generation allows the cross-sectional image of the separating portion of the large intestine region to be easily viewable from the viewpoint direction of the user.

Figure 6:
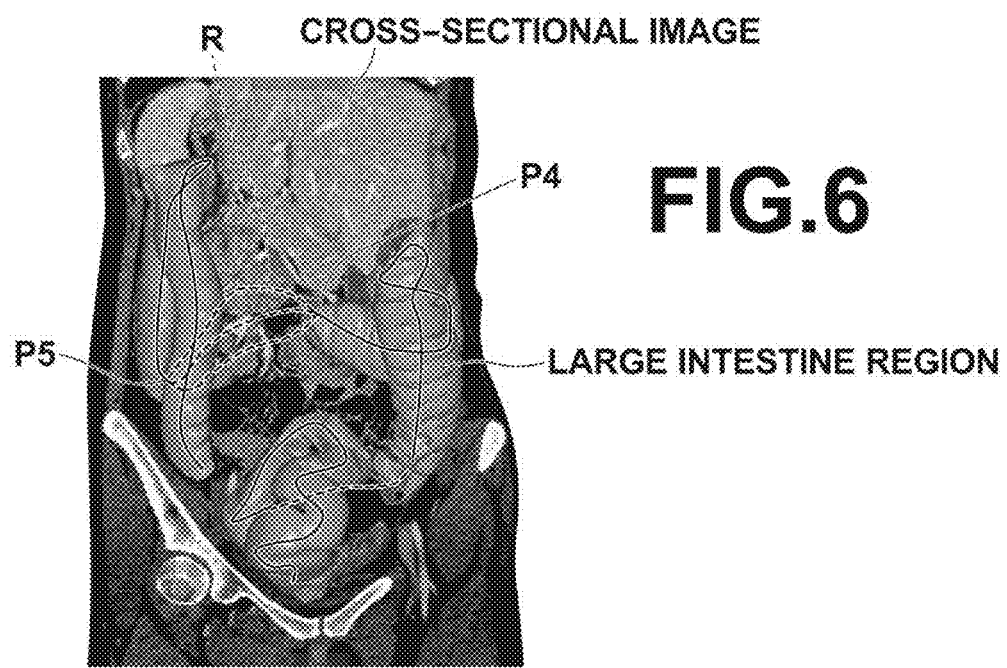
FIG. 6 is a drawing illustrating an example in which the three-dimensional large intestine image and the cross-sectional image are displayed on top of each other.

Then, the cross-sectional image generated by the cross-sectional image generation unit 14 is outputted to the display control unit 17, and the display control unit 17 displays the inputted cross-sectional image on the display 3 (S24). FIG. 6 shows an example in which the cross-sectional image that includes the endpoints P4 and P5 is displayed superimposed on the three-dimensional image of the large intestine region as described above.

Next, a route connecting the two separate large intestine regions is inputted in the cross-sectional image displayed on the display 3 by the user with the use of the input device 4, and the route receiving unit 15 obtains information of the inputted route (S26). More specifically, as shown in FIG. 6, within the range R of the large intestine region appearing in the cross-sectional image, a route connecting the endpoints P4 and P5 is inputted by the user, and the route receiving unit 15 receives the inputted route as a route connecting between the two separate large intestine regions. Then, the route receiving unit 15 outputs the information of the inputted route to the display control unit 17, and the display control unit 17 displays the route in the separating portion inputted by the user. Note that the input of route by the user is not limited to once and may input again after the inputted route is erased. That is, the user may edit the route by repeating the route input many times until a desired route is determined.

Then, when the route inputted by the user is finally determined, for example, by pressing a determination button (S28), the route receiving unit 15 outputs information of the final route to the virtual endoscopic image generation unit 16.

The virtual endoscopic image generation unit 16 obtains the endoscopic route obtained from the endoscopic route obtaining unit 12 and the route outputted from the route receiving unit 15 and obtains a final single endoscopic route by connecting these two routes, and generates a virtual endoscopic image based on the endoscopic route (S30). Note that the generation of the virtual endoscopic image may be implemented by moving the viewpoint along the final endoscopic route and sequentially generating a virtual endoscopic image at each viewpoint or by displaying the final endoscopic route on the display 3 and generating a virtual endoscopic image at a viewpoint on the displayed endoscopic route specified by the user with the use of the input device 4.

Then, the virtual endoscopic image generated by the virtual endoscopic image generation unit 16 is outputted to the display control unit 17 and the display control unit 17 displays the inputted virtual endoscopic image on the display 3 (S32).

According to the endoscopic image diagnosis support system of the foregoing embodiment, a large intestine region is extracted and obtained from a three-dimensional image of a subject, and if the obtained large intestine region is separated, each endpoint of the two large intestine regions connecting to the separating portion is identified, a cross-sectional image that includes the identified two endpoints is generated, then the generated cross-sectional image and the three-dimensional image of the large intestine region are displayed, and input of a route connecting between the two large intestine regions is received. This allows the user to input a route by understand the structure of the separating portion described above by the cross-sectional image, while understanding the three-dimensional structure of the large intestine region by viewing the three-dimensional image, whereby the user may edit the route in the separating portion easily and accurately.

In the foregoing embodiment, the description has been made of a case in which the endpoints P4 and P5 are selected by the user and a cross-sectional image that includes the endpoints P4 and P5 is generated. But, if the endpoints P2 and P3 are selected by the user, a cross-sectional image that includes the endpoints P2 and P3 is generated and the cross-sectional image is displayed superimposed on the three-dimensional image of the large intestine region. The method of generating the cross-sectional image is the same as that described above, an a cross-sectional image that includes the endpoints P2 and P3 and whose normal vector gives a maximum inner product with a normal vector of the projection plane of the three-dimensional image of the large intestine region. Then, a route connecting the two separate large intestine regions is inputted in the cross-sectional image by the user, whereby a new one endoscopic route is determined.

Further, in the foregoing embodiment, the endpoints P4 and P5, and the endpoints P2 and P3 are selected by the user, but they may be detected automatically. For example, an arrangement may be adopted in which an endpoint of the endoscopic route obtained by the endoscopic route obtaining unit is detected automatically by the endpoint identification unit 13.

Still further, in the foregoing embodiment, the description has been made of a case in which a planar cross-sectional image is generated as the cross-sectional image, as shown in FIG. 6, but the cross-sectional image is not limited to this and a CPR (Curved Planar Reformation) image may be displayed.

When displaying a CPR image, route information that serves as a core line in generating a CPR image is required. Therefore, when displaying a CPR image, a route connecting between two separate large intestine regions is inputted by the user before displaying the image. For example, in the example of the foregoing embodiment, a route connecting the endpoints P4 and P5 is inputted properly by the user.

Then, a CPR image is generated by the cross-sectional image generation unit 14 using the route inputted by the user in the manner described above as a core line, and the CPR image is displayed on the display 3 by the display control unit 17. As the CPR image generation method is already known as described, for example, in Japanese Unexamined Patent Publication No. 2012-024517, the detailed description will be omitted here.

Next, for example, if the user observing the CPR image displayed on the display 3 feels that the separating portion of the large intestine region is unclear in the currently displayed CPR image and thinks that the CPR image is not appropriate for inputting a correct endoscopic route, a route connecting the endpoints P4 and P5 is inputted again by the user and a CPR image is generated again using the route as a core line. Then, the regenerated CPR image is displayed by switching from the previous CPR image. In this way, the route input by the user and the CPR image display with the route as a core line are repeated and a final route is determined.

Further, in the foregoing embodiment, the three-dimensional image of the large intestine region and the cross-sectional image are displayed superimposed on top of each other, but not limited to this, the three-dimensional image of the large intestine region and the cross-sectional image may be displayed side-by-side. In particular, in the case in which a plurality of separating portions are present, as shown in FIG. 3, a side-by-side display of cross-sectional images of the plurality of separating portions, for example, a cross-sectional image that includes the endpoints P4 and P5, and a cross-sectional image that includes the endpoints P2 and P3 may provide better overview.

Figure 7:
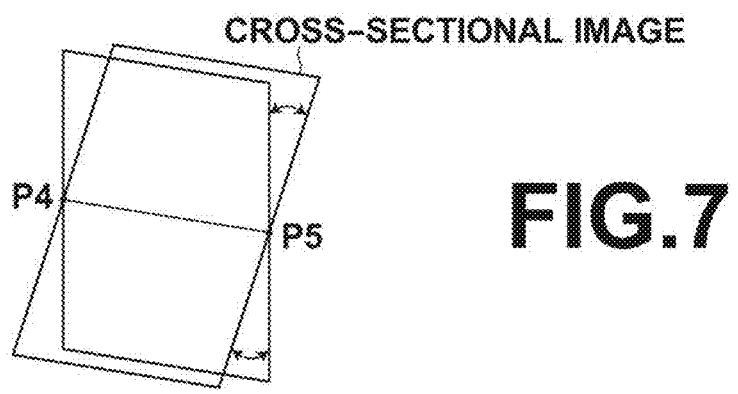
FIG. 7 is a drawing for explaining another cross-sectional image generation method.
Figure 8:
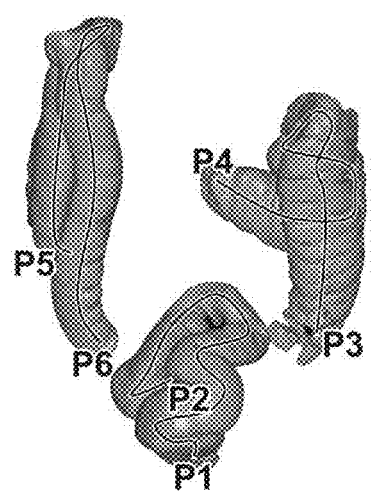
FIG. 8 is a drawing for explaining an example in which a large intestine region is extracted as a plurality of separate regions.

Still further, in the foregoing embodiment, when generating a cross-sectional image, a cross-sectional image that includes two endpoints and whose normal vector gives a maximum inner product with a normal vector of the projection plane of the three-dimensional image of the large intestine region is generated. But the determination method of the cross-sectional image is not limited to this and, for example, an arrangement may be adopted in which a plurality of cross-sectional images, each including two endpoints, is generated, then the plurality of cross-sectional images is displayed on the display 3 to allow the user to select an appropriate one from the plurality of cross-sectional images, and the cross-sectional image selected by the user is displayed superimposed on the three-dimensional image of the large intestine region. Alternatively, an arrangement may be adopted in which a plurality of cross-sectional images, each including two endpoints, is generated as in the above, as shown in FIG. 7, then the plurality of cross-sectional images is switched and displayed by rotating them with the straight line connecting the two endpoints as the axis, and an appropriate one is selected by the user from the plurality of switched and displayed cross-sectional images. Further, the switching of the cross-sectional images may also be performed by the user with the use of a mouse or the like.

What is claimed is:

1. A medical image display apparatus, comprising:
a three-dimensional image obtaining unit that obtains a three-dimensional image of a subject;
a tubular tissue region obtaining unit that obtains a tubular tissue region representing a tubular tissue of the subject from the three-dimensional image obtained by the three-dimensional image obtaining unit;
an endpoint identification unit that identifies, if the tubular tissue region obtained by the tubular tissue region obtaining unit is separated, each endpoint of the two tubular tissue regions connecting to the separating portion;
a cross-sectional image generation unit that generates a cross-sectional image that includes the two endpoints identified by the endpoint identification unit;
a display control unit that displays the cross-sectional image generated by the cross-sectional image generation unit and a three-dimensional image of the tubular tissue region; and
a route receiving unit that receives input of a route connecting between the two tubular tissue regions.

2. The medical image display apparatus as claimed in claim 1, wherein the cross-sectional image generation unit generates a cross-sectional image whose normal vector gives a maximum inner product with a normal vector of a projection plane of the three-dimensional image of the tubular tissue region.

3. The medical image display apparatus as claimed in claim 1, wherein the endpoint identification unit identifies points inputted by the user using an input device as the two endpoints.

4. The medical image display apparatus as claimed in claim 1, wherein the endpoint identification unit automatically detects and identifies the two endpoints.

5. The medical image display apparatus as claimed in claim 1, wherein the display control unit displays the cross-sectional image and the three-dimensional image of the tubular tissue region superimposed on top of each other.

6. The medical image display apparatus as claimed in claim 1, wherein the display control unit displays the cross-sectional image and the three-dimensional image of the tubular tissue region side-by-side.

7. The medical image display apparatus as claimed in claim 1, wherein the cross-sectional image generation unit generates, as the cross-sectional image, a CPR (Curved Planar Reformation) image using the route received by the route receiving unit as a core line.

8. The medical image display apparatus as claimed in claim 7, wherein:
the route receiving unit receives the input of a route connecting the two tubular tissue regions a plurality of times; and
the cross-sectional image generation unit generates a CPR image with respect to each input of a route.

9. The medical image display apparatus as claimed in claim 1, wherein the tubular tissue region is a large intestine, a small intestine, a bronchus, or a blood vessel.

10. A medical image display method, comprising the steps of:
obtaining a three-dimensional image of a subject;
obtaining a tubular tissue region representing a tubular tissue of the subject from the obtained three-dimensional image;
if the obtained tubular tissue region is separated, identifying each endpoint of the two tubular tissue regions connecting to the separating portion;
generating a cross-sectional image that includes the identified two endpoints;
displaying the generated cross-sectional image and a three-dimensional image of the tubular tissue region; and
receiving input of a route connecting between the two tubular tissue regions.

11. A non-transitory computer-readable recording medium containing a medical image display program for causing a computer to function as:
a three-dimensional image obtaining unit that obtains a three-dimensional image of a subject;
a tubular tissue region obtaining unit that obtains a tubular tissue region representing a tubular tissue of the subject from the three-dimensional image obtained by the three-dimensional image obtaining unit;
an endpoint identification unit that identifies, if the tubular tissue region obtained by the tubular tissue region obtaining unit is separated, each endpoint of the two tubular tissue regions connecting to the separating portion;
a cross-sectional image generation unit that generates a cross-sectional image that includes the two endpoints identified by the endpoint identification unit;
a display control unit that displays the cross-sectional image generated by the cross-sectional image generation unit and a three-dimensional image of the tubular tissue region; and
a route receiving unit that receives input of a route connecting between the two tubular tissue regions.

* * * * *